United States Patent
Fukushima et al.

(10) Patent No.: US 7,326,580 B2
(45) Date of Patent: Feb. 5, 2008

(54) METHOD OF OBSERVING MONOLAYER ULTRAVIOLET DECOMPOSITION PROCESS, METHOD OF CONTROLLING DEGREE OF SURFACE DECOMPOSITION, AND PATTERNING METHOD

(75) Inventors: Hitoshi Fukushima, Nagano-ken (JP); Masaya Ishida, Nagano-ken (JP); Stephen Evans, University of Leeds (GB); Kevin Critchley, University of Leeds (GB)

(73) Assignee: Seiko Epson Corporation, Tokyo (JP)

( * ) Notice: Subject to any disclaimer, the term of this patent is extended or adjusted under 35 U.S.C. 154(b) by 472 days.

(21) Appl. No.: 10/913,523

(22) Filed: Aug. 9, 2004

(65) Prior Publication Data
US 2005/0244588 A1 Nov. 3, 2005

(30) Foreign Application Priority Data
Apr. 30, 2004 (GB) ................. 0409701.0

(51) Int. Cl.
*H01L 21/00* (2006.01)
(52) U.S. Cl. .......................... 438/7; 438/16
(58) Field of Classification Search ............ 438/7, 438/16
See application file for complete search history.

(56) References Cited

U.S. PATENT DOCUMENTS 4,670,650 A 6/1987 Matsuzawa et al.
5,837,744 A 11/1998 Nagashima et al.

FOREIGN PATENT DOCUMENTS

JP A 10-206357 8/1998

OTHER PUBLICATIONS

Hong et al., "Micropatterning of organosilane self-assembled monolayers using vacuum ultraviolet light at 172nm: resolution evaluation by Kelvin-probe force microscopy", Surface and Coatings Technology 169-170 (2003), pp. 211-214.*
Atsushi Hozumi et al., "Amino-terminated self-assembled monolayer on a $SiO_2$ surface formed by chemical vapor deposition," J. Vac Sci. Technol. A 19(4), Jul./Aug. 2001, pp. 1812-1816.
Hiroyuki Sugimura et al., "Micropatterning of Alkyl- and Fluoroalkylsilane Self-Assembled Monolayers Using Vacuum Ultraviolet Light", Langmuir 2000, 16, pp. 885-888.
Anthony J. Wagner et al., "X-ray Induced Modification of Semifluorinated Organic Thin Films", J. Phys. Chem. B 2000, 104, pp. 3291-3297.

* cited by examiner

*Primary Examiner*—Richard A. Booth
(74) *Attorney, Agent, or Firm*—Oliff & Berridge, PLC

(57) ABSTRACT

Aspects of the invention can provide a method of effectively observing the photodecomposition process of a monolayer in real time. The invention can provide a method of observing the decomposition process of a monolayer when the monolayer is irradiated with UV rays, where the structure of the constituent molecule of the monolayer in an ultrahigh vacuum atmosphere and an oxygen-containing atmosphere respectively can be measured by a molecular structure measuring device during the UV irradiation. The invention can also provide a method of controlling the degree of surface decomposition of the monolayer that controls the ozone concentration accompanying the UV irradiation based on observation results obtained by using the observation method. The invention can further provide a method of patterning the monolayer that employs the control method.

8 Claims, 11 Drawing Sheets

METHOD OF OBSERVING MONOLAYER ULTRAVIOLET DECOMPOSITION PROCESS, METHOD OF CONTROLLING DEGREE OF SURFACE DECOMPOSITION, AND PATTERNING METHOD

BACKGROUND OF THE INVENTION

1. Field of Invention

Aspects of the invention can relate to a method of observing a monolayer ultraviolet decomposition process that allows real-time information relating to the monolayer surface reaction to be obtained in a straightforward manner when monolayer decomposition patterning is performed by ultraviolet rays, as well as to a method of controlling the degree of monolayer surface decomposition and a patterning method that employ this observation method.

2. Description of Related Art

Attempts to control the surface physical properties of a substrate or the like by using a self-assembled monolayer (SAM) have been increasingly used in industrial process applications. See, for example, A. Hozumi et al, J. Vac. Sci. Technol. A-Vac. Surf. Films 2001, 19, 1812, and H. Sugimura et al, Langmuir 2000, 16, 885, and so forth. For example, in order to control the adhesion of a substrate surface or other surfaces, the work function of an electrode interface, the wettability, and so forth, a functional SAM is fixed to the surface of a variety of substrates, such as glass, semiconductor oxide substrate, plastic, aluminum oxide. Further, a multiplicity of silane compounds are used for the functional SAM used in this fixing process.

More particularly, a fluorinated silane compound whose end is substituted by a saturated fluorine chain, are effective materials for controlling surface energy and wettability. These fluorinated silane compounds are more particularly used frequently when surface patterning is performed by means of an SAM.

When patterning is performed by using a SAM, a method that causes a UV exposure unit to perform photodecomposition by irradiating a masked SAM surface with ultraviolet rays (UV), is used. Further, for the UV irradiation, optical energy with a wavelength of 173 nm is normally employed. Here, the SAM surface, which is irradiated with UV for a certain time, can be converted from a hydrophobic surface into a hydrophilic surface.

SUMMARY OF THE INVENTION

However, with related methods, a large amount of energy and time are required for the SAM photodecomposition process. For example, although a SAM consisting of a fluorinated silane compound formed on a silicon substrate decomposes during UV irradiation with a wavelength of 173 nm, the injection energy at such time is extremely large but the majority of this energy is emitted as heat energy.

For this reason, an improvement for the efficient promotion of the SAM UV decomposition process is required. However, because the photodecomposition process and mechanism are unknown, there has been uncertainty with regard to which chemical species is produced at the surface of the SAM and whether decomposition is progressing. In addition, there has been no method of observing effectively the decomposition process in real time.

Accordingly, an aspect of the invention can provide a method of observing effectively the monolayer photodecomposition process in real time.

The invention can provide a method of observing the decomposition process of a monolayer when the monolayer is irradiated with UV rays, such that the structure of the constituent molecule of the monolayer in an ultrahigh vacuum atmosphere and an oxygen-containing atmosphere respectively is measured by a molecular structure measuring device during the UV irradiation.

The invention can also provide the observation method, control method and patterning method outlined described below. The observation method described above, where the molecular structure measuring device are means that employ X-rays. Further, the observation method described above, where the wavelength of the UV rays is 174 nm or more.

Additionally, the observation method described above can include that the monolayer is a self-assembled monolayer. The observation method described above can also include that the constituent molecule of the monolayer is a compound terminated by a fluorine chain. Also, the above observation method can include that a physical property of the surface of the monolayer is also measured before and after the UV irradiation. The observation method can further have that the surface physical property is the surface potential, thickness or wetting contact angle (water).

The invention can further provide a method of controlling the degree of surface decomposition of the monolayer where the ozone concentration accompanying the UV irradiation is controlled based on observation results obtained by using the observation method described above. Further, a method of patterning a monolayer, can employ the control method described above.

The invention can provide a method of observing effectively the monolayer photodecomposition process in real time. Further, the degree of surface decomposition of the monolayer can be controlled by controlling the ozone concentration accompanying to the UV irradiation based on observation results obtained by means of this method. Further, photodecomposition patterning of the monolayer by means of UV rays can be efficiently performed based on information on the photodecomposition process that is obtained by means of this observation method. This is particularly useful in a case where the surface is afforded hydrophilicity by selectively cleaving the C—F bond of a fluorine chain when a fluorine-chain-containing SAM is subjected to decomposition patterning by means of UV photo-irradiation.

BRIEF DESCRIPTION OF THE DRAWINGS

The invention will be described with reference to the accompanying drawings, wherein like numerals reference like elements, and wherein.

DETAILED DESCRIPTION OF PREFERRED EMBODIMENTS

Figure 1:
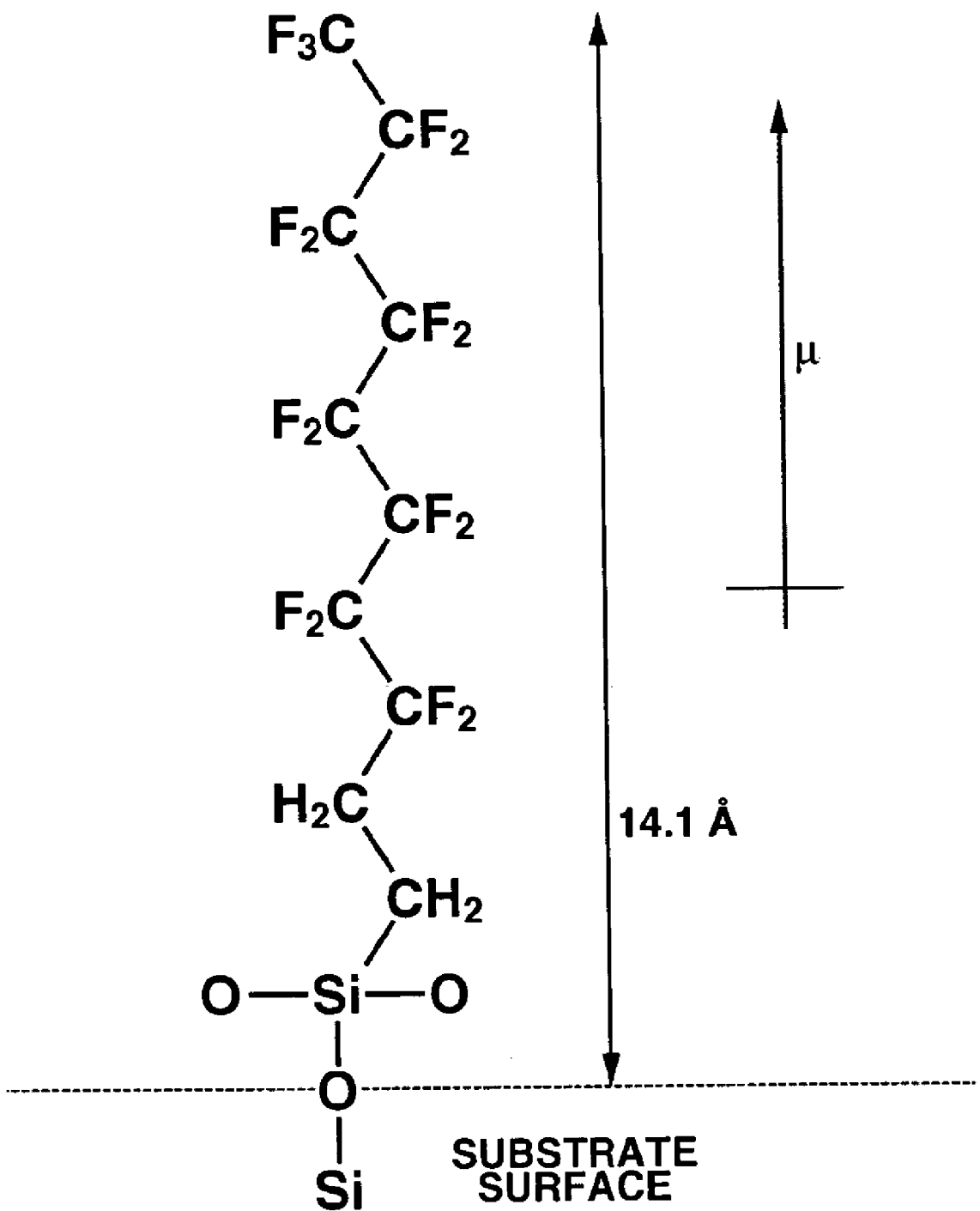
FIG. 1 shows a silane compound (a structural formula) with a fluorine chain, which is one example of a compound constituting an SAM on a substrate surface.

The invention will be described hereinbelow based on preferred exemplary embodiments.

The observation method of the monolayer decomposition process according to the invention can include a method of observing the decomposition process of a monolayer when the monolayer is irradiated with UV rays, characterized in that the structure of the constituent molecule of the monolayer in an ultrahigh vacuum atmosphere and an oxygen-containing atmosphere respectively is measured by molecular structure measuring means during the UV irradiation.

By virtue of having this constitution, the observation method of the present invention is capable of observing the monolayer photodecomposition process immediately and effectively in real time.

The molecular structure measuring means employed by the method of the present invention are not particularly limited. Possible means include means that employ X-rays, means that use infrared rays, UV rays, visible light, and so forth, for example. However, means that employ X-rays are particularly preferable by virtue of permitting effective observation. Examples of means that employ X-rays suitably include XPS (X-ray photoelectron spectroscopy) devices and systems, and so forth, for example.

Provided that the monolayer decomposition reaction can be induced, the UV rays (ultraviolet light: UV) that constitute the light source used by the method of the present invention are not especially restricted in terms of the wavelength and output thereof, and so forth. However, more particularly, the wavelength is preferably 174 nm or more due to the fact that such a wavelength permits the elimination of energy loss and an efficient process, and so forth. In the case of the present invention, this is desirable because enhanced results are prominent when ultraviolet light in a wavelength band between 174 nm and 400 nm in particular is used.

Possible light sources for irradiation with UV rays (ultraviolet light) include a secondary high-frequency light source such as a mercury lamp, a metal halide lamp, a 222 nm or 308 nm excimer light source, a KrF excimer light source, or an NdYAG laser. By using such light sources monolayer decomposition and patterning are feasible within a comparatively short irradiation time is feasible.

In the case of the method of the invention, measurements in the environments of an ultrahigh vacuum atmosphere and an oxygen-containing atmosphere respectively are performed separately. Here, an ultrahigh vacuum atmosphere is an environment where the influence of ozone generation is not substantial when UV irradiation is performed, 10-4 torr or less being preferable, and 10-5 to 10-8 torr being particularly preferable normally. On the other hand, an oxygen-containing atmosphere is an environment in which ozone can be generated by means of UV irradiation. For example, although such environments may include an and air, and so forth, an oxygen-containing nitrogen stream is particularly preferable.

In the method of the present invention, a monolayer targeted for decomposition-process observation, which is formed on a substrate (substrate surface), is normally used. Materials of a base for forming this monolayer may include an Si wafer (silicon substrate), quartz, quartz glass, glass, plastic film, a metal substrate, and so forth. A variety of base shapes can be used, such as a plate-like base or a curved body with a spherical curved surface or the like.

Monolayers include so-called monolayers such as organic molecular films deposited on a base, and, more particularly, organic compound ultrathin films, and, of these, self-assembled monolayers (SAM) are preferable for the following reasons. That is, a self-assembled monolayer is a film that consists of a binding functional group capable of reacting with the constituent atoms of an underlayer such as a substrate, or the like, and of other straight chain molecules, and in which a compound with extremely high directivity is oriented and formed by means of the mutual action of these straight chain molecules. The self-assembled film differs from the resin film of a photoresist or the like by virtue of being formed with oriented monomers. Therefore, the film thickness of a self-assembled film can be made very thin and the film is uniform at the molecular level. That is, because the same molecules are located at the surface of the film, it is possible to afford surface characteristics such as a uniform film surface, highly superior fluid repellency, lyophilicity, and so forth, which is particularly useful when performing detailed patterning.

The film thickness of the monolayer is determined by the length of the molecular chain, which is normally about 1 nm or less, at which the thickness is about 3 nm. This is on an entirely different scale to the resist film that is conventionally used in photolithography.

There are no particular restrictions on the compound for forming the monolayer, a variety of which can be used. However, in the observation method of the invention, usage of a compound terminated by a fluorine chain is especially preferable because contaminant molecules do not readily adhere to such a compound and thus surface reliability is ensured.

Of those compounds terminated by a fluorine chain, silane compounds terminated by a fluorine chain are particularly preferable because such compounds afford a stable chemical bond to a base such as a silicon substrate. In a silane compound, the part where the fluorine chain is present is the fluid-repellant part.

Suitable compounds for forming the monolayer can include, for example, silane compounds with a fluorine chain such as fluoroalkylsilanes (hereinafter called 'FAS'), such as perfluoroalkyltrialkoxysilane, heptadecafluoro-tetrahydrodecyl-triethoxy-silane, heptadecafluoro-tetrahydrodecyl-trichlorosilane, tridecafluorotetrahydrooctyl-trichlorosilane, and trifluoropropyl-trimethoxysilane. More particularly, when a fluoroalkylsilane (FAS) is used, because a self-assembled film is formed with each compound oriented so that the fluoroalkyl group is located at the surface of the film, the surface of the film is afforded uniform fluid repellency. In practice, usage of one compound by itself is also preferable. However, two or more types of compounds may also be combined and used, there being no restrictions as long as the effects of the invention are not compromised.

Alkylsilanes with an alkyl group can also be employed as materials other than silane compounds with a fluorine chain. In comparison with fluoroalkyl groups, alkyl groups are inferior in terms of their water repellency and repellant ink characteristics but can be adequately used in patterning processes.

It is understood that monolayers with a variety of functional groups other than compounds with FAS or other fluorine chains are effective in the application of the observation method of the present invention.

Furthermore, in the case of the invention, the monolayer photodecomposition process is observed by comparing the results of measuring the structure of the constituent molecule of the monolayer during UV irradiation in an ultrahigh vacuum atmosphere with the results of measuring the structure of the constituent molecule of the monolayer in an oxygen-containing atmosphere.

The method of the invention preferably can include a step of measuring a physical property of the surface of the monolayer before and after the UV irradiation in addition to the molecular structure measurement step because information relating to the surface reaction of the monolayer is more effectively obtained in this manner.

The physical property of the surface of the monolayer that is measured in this step is preferably the surface potential, thickness, or wetting contact angle (water) because useful information for particularly efficient patterning is thus obtained.

The invention can also be provided in the form of a system other than that of a device that employs this observation method for a monolayer decomposition process.

The method of controlling the degree of surface decomposition of the monolayer according to the present invention is characterized in that the ozone concentration accompanying the UV irradiation is controlled based on observation results obtained by using the above-mentioned observation method.

By virtue of having this constitution, the control method according to the invention is capable of effectively controlling the degree of surface decomposition of the monolayer, and thus makes it possible to perform efficient patterning of the monolayer as well as control of function processing for a functional thin film, such as an SAM in a straightforward manner.

The invention can also be provided in the form of a system other than that of a device that employs this method of controlling the degree of surface decomposition of the monolayer.

The method of patterning a monolayer according to the invention is characterized in that the control method is employed. By virtue of having this constitution, the patterning method of the invention is capable of efficiently patterning the monolayer.

The invention can also be provided in the form of a system other than that of a device that employs this method of patterning the monolayer.

The invention will be described hereinbelow more specifically by presenting exemplary embodiments of the invention by way of example. However, it should be understood that the invention is not limited in any way whatsoever by such embodiments.

First, for an FAS-SAM, a SAM, which consists of a silane compound containing a fluorine chain shown in FIG. 1 (perfluorodecyltriethoxysilane), is provided on a silicon substrate and then undergoes UV irradiation with a wavelength of 254 nm. This decomposition process was observed in its respective environments.

Photodecomposition was performed by allowing UV light (UV photo-irradiation energy with a wavelength of 254 nm) to pass through a transparent window made of silica to irradiate a silane SAM of a substrate surface. UV light with a wavelength of 254 nm was used because ozone, which accelerates photodecomposition by means of UV light with a long wavelength of 254 nm more than the 174 nm of the wavelength of a high-energy light source, is generated. At the same time, an XPS (X-ray photoelectron spectroscopy) measurement is carried out during the photo-irradiation in an ultrahigh vacuum, and it was observed under what influence an SAM material not afforded the property of absorption in the UV wavelength band underwent UV decomposition in the absence of oxygen.

In addition, in a state where the chamber was filled with nitrogen (including oxygen), UV light was similarly irradiated and the decomposition process of the SAM surface was measured. The results for both environments were then compared.

Figure 2:
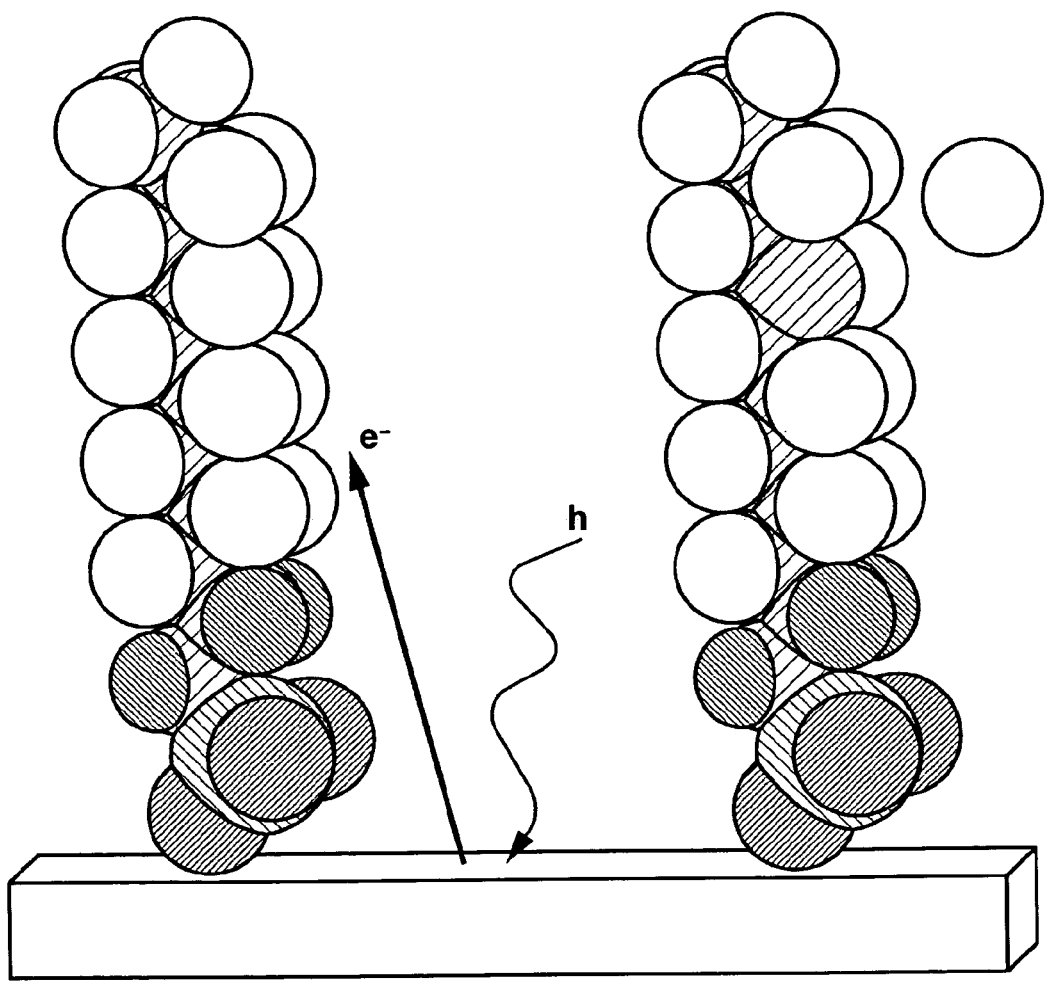
FIG. 2 schematically shows an aspect of cleavage of a C—F bond when the SAM is irradiated with UV rays in an ultrahigh vacuum atmosphere.
Figure 3:
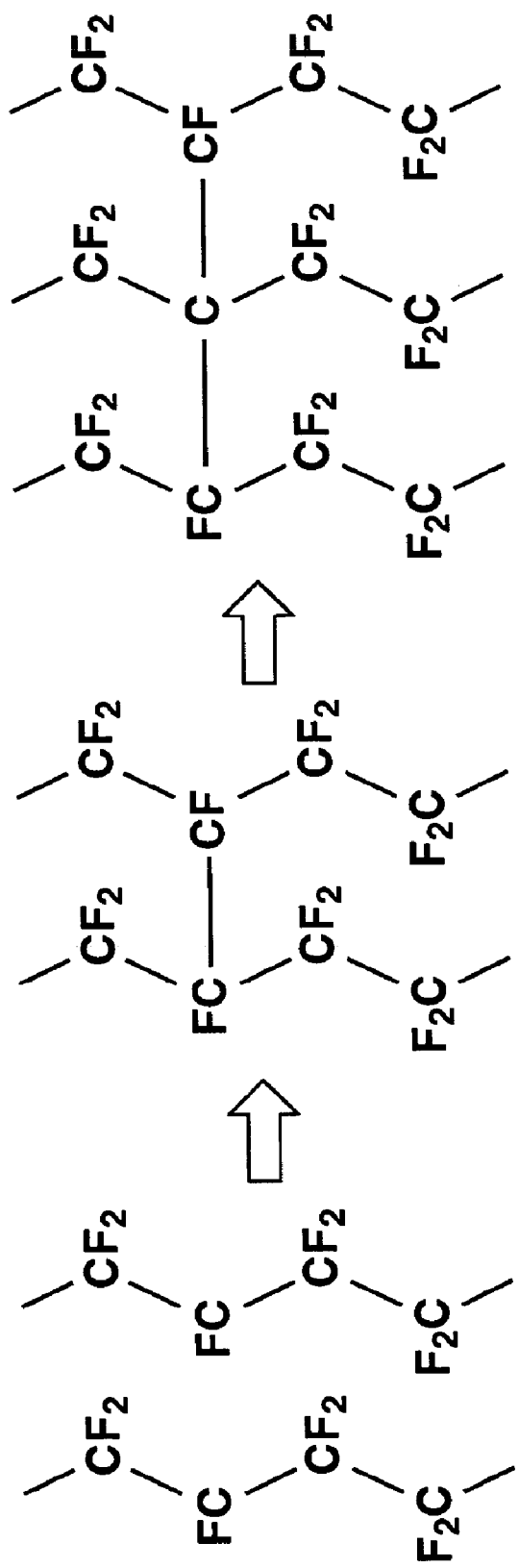
FIG. 3 shows, as a structural formula, an aspect in which an intermolecular CF—CF bond resulting from the recombination of CF radicals following cleavage of the C—F bonds in FIG. 2 is formed.

That is, with the absence of ozone as a condition (in an ultrahigh vacuum atmosphere), as shown in FIG. 2, the CF bond was mainly cleaved and the CF2-CF2 bond was easily broken. Further, as shown in FIG. 3, after the CF bond was cleaved, there was a high possibility of CF radicals recombining to form intermolecular CF—CF bonds (see Wanger A J, Han K., J. Phy. Chem. B, 2000, 104, 3291). Under this condition, the fluorine atom decomposition efficiency overall was poor.

Figure 4:
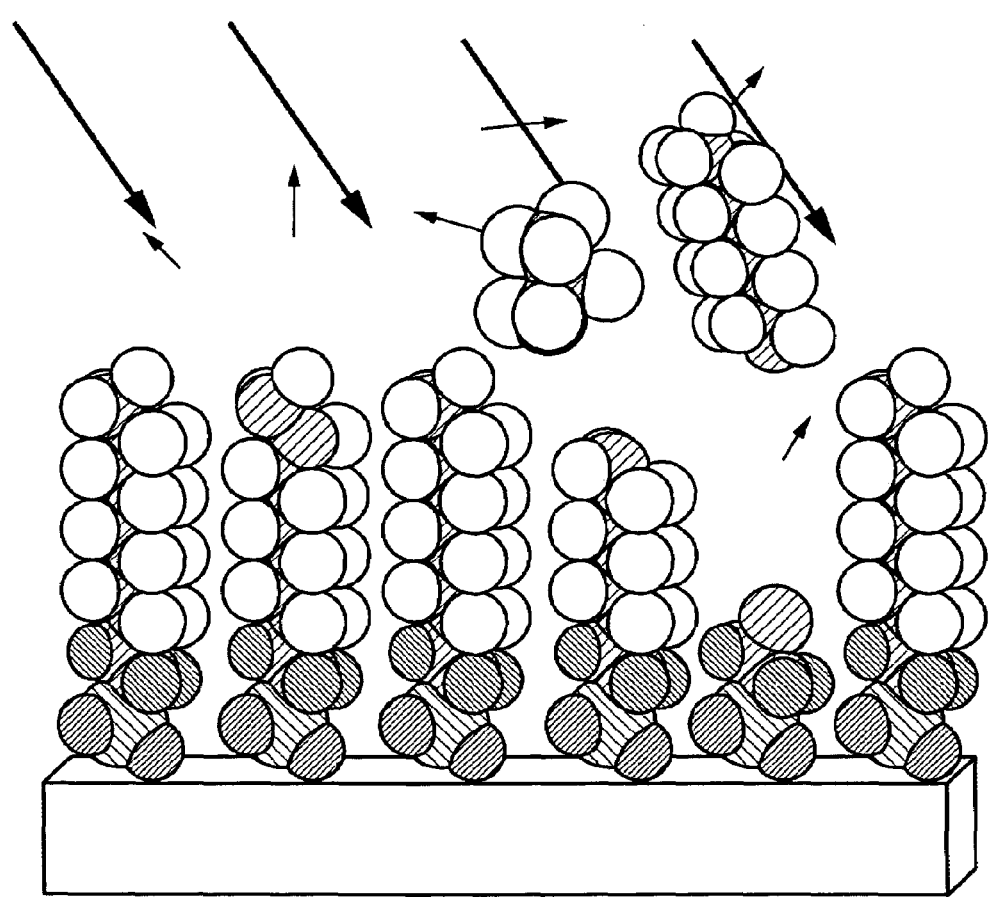
FIG. 4 is a schematic diagram showing an aspect in which both the C—F and CF2-CF2 bonds when a SAM is irradiated with UV rays in an oxygen-containing atmosphere are cleaved.

On the other hand, as shown in FIG. 4, when the same UV exposure as above was performed in an oxygen-containing nitrogen stream, large quantities of the CF and the CF2-CF2 bonds alike were cleaved in a short time, and the rate of reduction of the fluorine atoms from the SAM surface was high. As a result, it was established that the extent of UV decomposition of the SAM surface could be controlled by effectively controlling the ozone concentration (oxygen concentration).

Next, an evaluation involving measurement of the surface potential, ellipsometry, and contact angle was performed on the SAM surface before and after the UV reaction. Information relating to the SAM surface reaction was then effectively obtained by combining the evaluation results with decomposition process measurements (the results of real-time observation).

A monolayer consisting of an FAS-SAM is created by a conventional method on the surface of a silicon substrate. The FAS-SAM is formed from perfluorodecyltriethoxysilane. That is, an FAS stock solution is placed along with a silicon substrate within a hermetically sealed chamber whose internal temperature can be controlled. Thereafter, the internal temperature is raised to 150° C. and the FAS vaporization is adjusted to reach saturation point. After about two hours, the substrate is removed and the surface thereof is washed using dichloromethane or chloroform, or the like, before being dried in nitrogen and provided for use in a UV irradiation experiment described subsequently. Here, where the initial surface physical property of the monolayer consisting of an FAS-SAM formed on a substrate is concerned, the wetting contact angle was 119 degrees with respect to the angle of advance and 96 degrees with respect to the receding angle (water).

First, measurements were made before and after UV irradiation to determine to what extent the wettability, thickness and surface potential of the FAS-SAM surface had changed.

Figure 6:
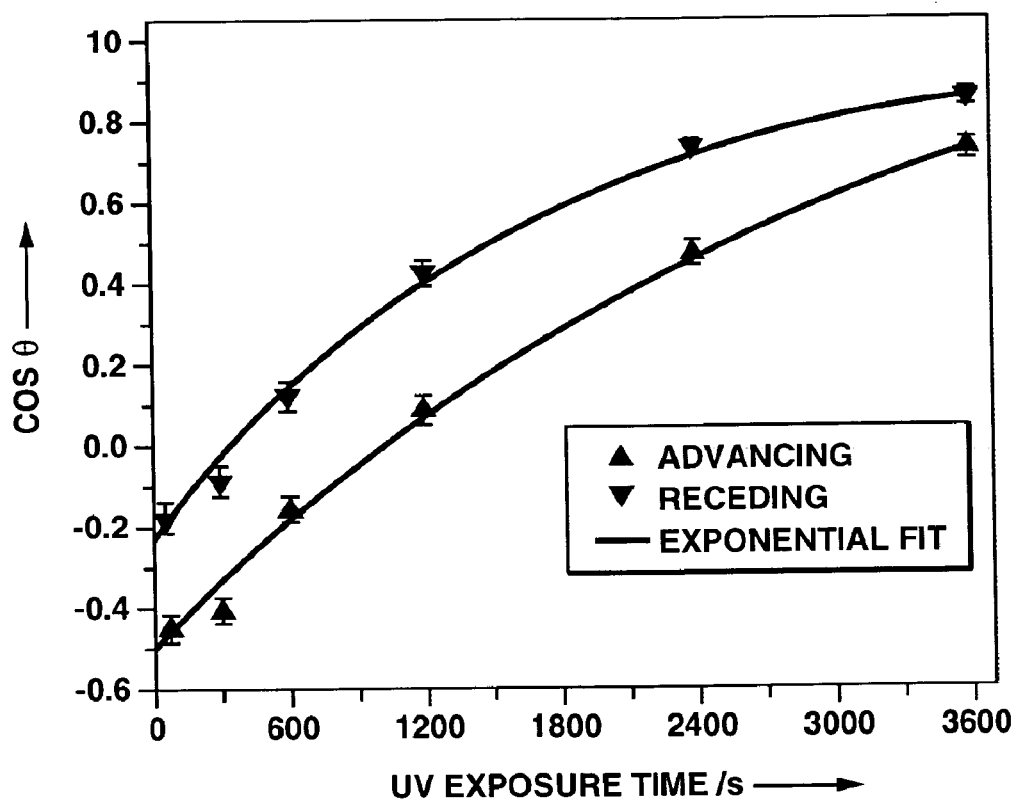
FIG. 6 is a graph showing the change in wettability, which is a physical property of the surface of an FAS-SAM, with respect to the UV irradiation time.

FIG. 6 is a graph showing the change in wettability, which is a physical property of the surface of the FAS-SAM, with respect to the UV irradiation time. The wettability is converted to a numerical value by rendering the theta value obtained by means of the contact angle measurement (wetting contact angle (water)) cos θ. As shown in FIG. 6, the wetting contact angle exhibits a decrease (cos θ increases), which indicates a drop in the water repellency of the FAS-SAM.

Figure 7:
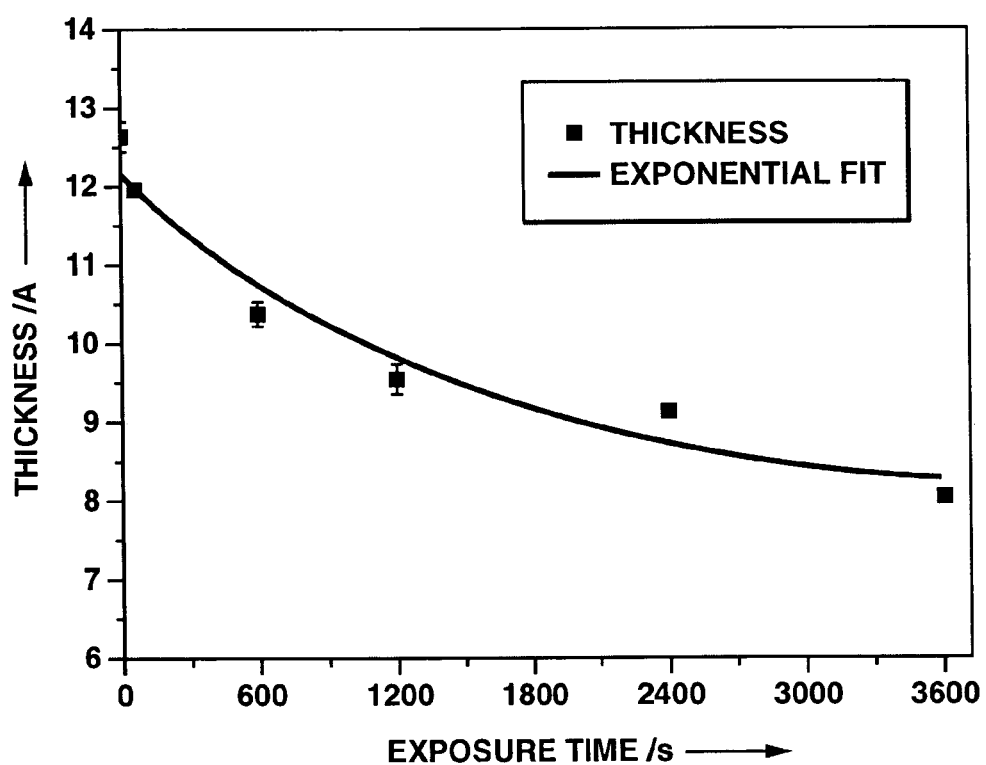
FIG. 7 is a graph showing the change in the thickness of the FAS-SAM with respect to the UV irradiation time.

FIG. 7 is a graph showing the change in the thickness of the FAS-SAM with respect to the UV irradiation time. The thickness is based on data measured by means of ellipsometry. It is known that the thickness of the FAS-SAM also decreases in accordance with the UV irradiation, as shown in FIG. 7.

Figure 8:
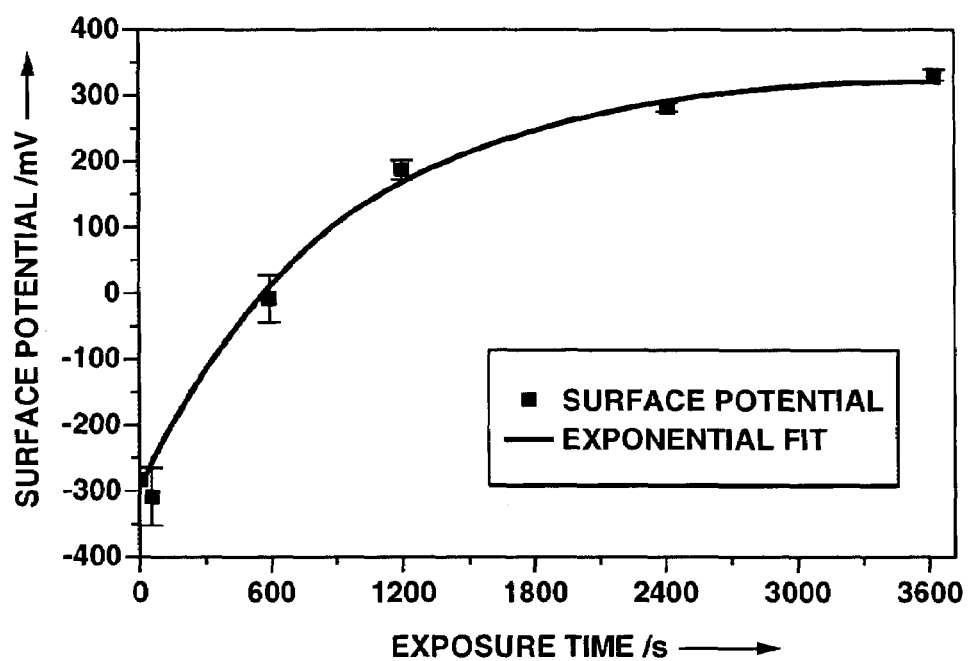
FIG. 8 is a graph showing the change in the surface potential of the FAS-SAM with respect to the UV irradiation time.

FIG. 8 is a graph showing the change in the surface potential of the FAS-SAM with respect to the UV irradiation time. Measurement of the surface potential was performed by using a Kelvin probe. As shown in FIG. 8, with respect to the value of the surface potential, an initial minus potential peculiar to fluorine of the FAS-SAM changes to a positive potential after UV irradiation. That is, this change indicates fluorine-chain reduction and separation.

Next, analysis was performed by means of XPS in an oxygen-containing nitrogen stream.

Figure 5:
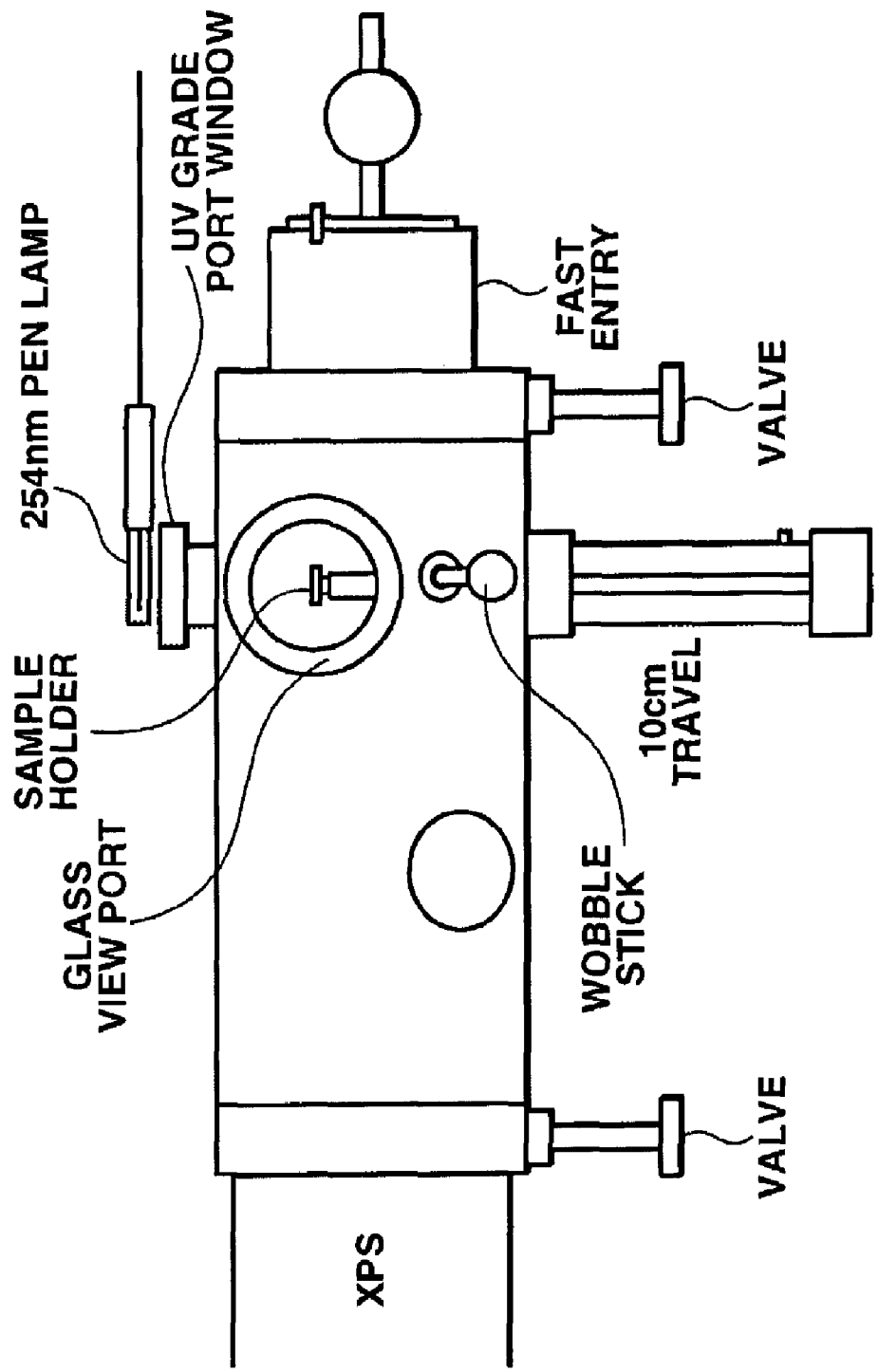
FIG. 5 is an outline constitutional view of part of a device (XPS) used in the observation method of the exemplary embodiment.

In this exemplary embodiment, the device shown in FIG. 5 was used in the XPS to measure the structure of the constituent element of the FAS-SAM during UV irradiation when this SAM was irradiated with UV. Further, FIG. 5 is an outline constitutional view of part of the device used in the observation method of the present embodiment. As FIG. 5 shows, this measurement device comprises a chamber, which is a measurement space that permits the setting of environments such as an ultrahigh vacuum atmosphere and an oxygen-containing atmosphere; a sample holder for installing an FAS-SAM-formation substrate constituting a sample within this chamber; a UV lamp for providing UV irradiation via quartz glass, which is positioned above the substrate; and a window that allows the state of the SAM during UV irradiation to be observed.

The UV lamp performs UV irradiation with a wavelength of 254 nm and has an output of 7 mW/cm2. The FAS-SAM surface was subjected to UV irradiation and surface measurements were taken in real time by means of XPS for each irradiation interval.

Figure 9:
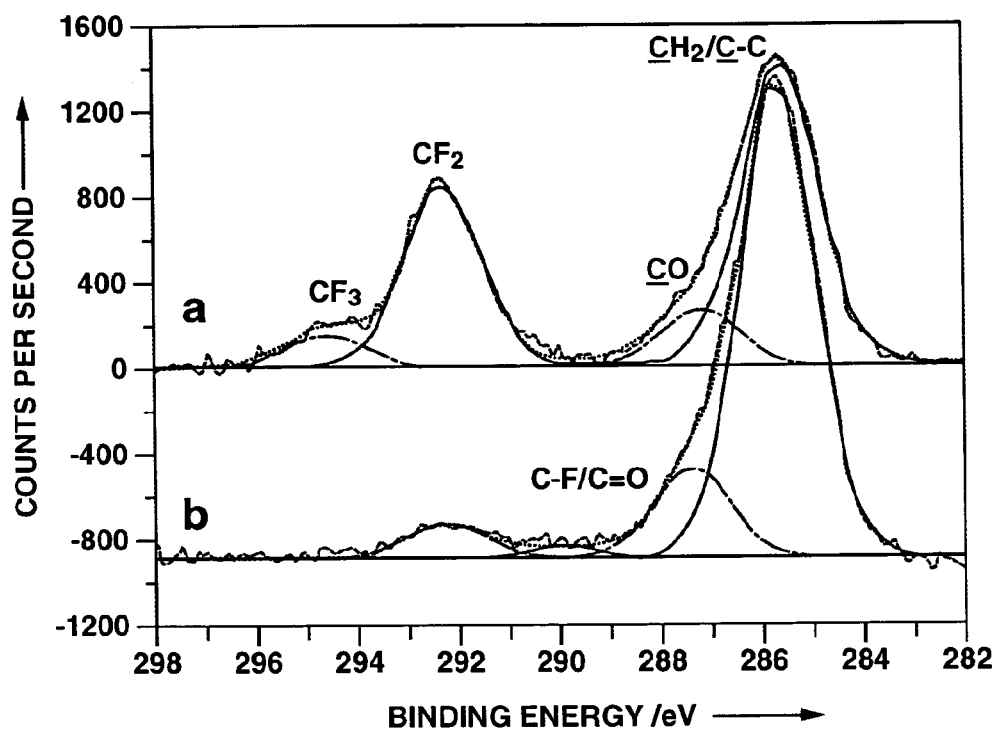
FIG. 9 is a graph showing data measured by means of XPS, immediately before UV irradiation (a) and after UV irradiation for one hour (b) in an oxygen-containing nitrogen stream.

FIG. 9 is a graph showing data measured by XPS immediately before UV irradiation (a) and after UV irradiation for one hour (b) in an oxygen-containing nitrogen stream. As FIG. 9 shows, a comparison of the data immediately before UV irradiation and after UV irradiation for one hour first clearly identified a reduction of fluorine atoms and CF2 bond units and that there was, at the same time, an increase in the proportion of CH2 bond units. Further, because CF3 units substantially disappear, there is a high possibility of cleavage of the CF3-CF2 bonds.

Figure 10:
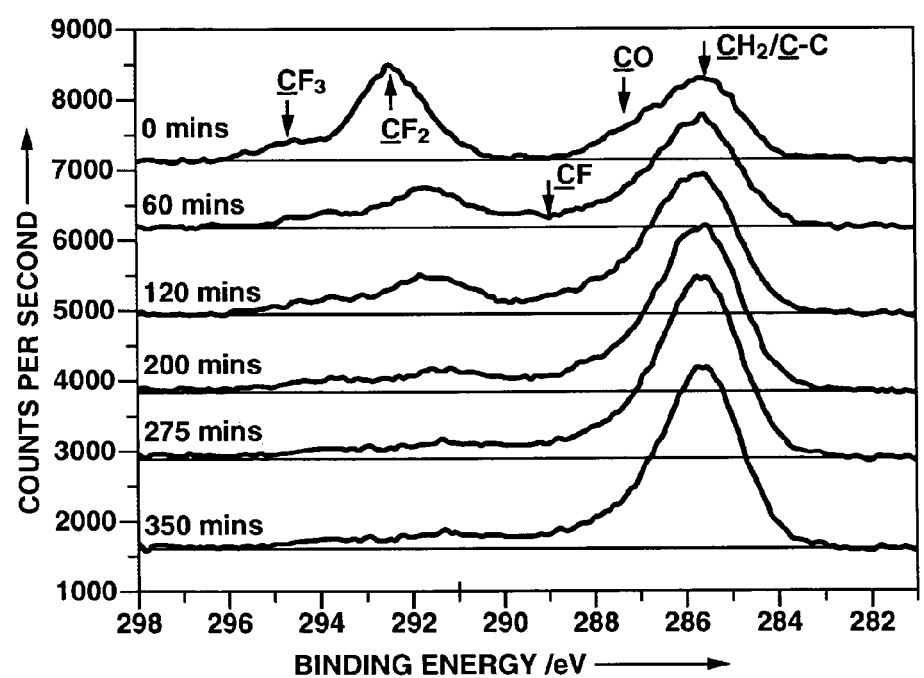
FIG. 10 is a graph showing the change in the per-second binding energy of C with respect to the UV irradiation time.

Further, a UV irradiation experiment was similarly performed with the inside of the chamber of the measurement device shown in FIG. 5 in an ultrahigh vacuum state (at 10-8 mBar or less). FIG. 10 is a graph showing the change in the per-second binding energy of C with respect to the UV irradiation time. As FIG. 10 shows, similarly, after irradiation for one hour, the conversion of the CF2 bond units to a CF bond state (that is, only one fluorine atom is removed from the carbon and exists in the CF bond state) can be discerned from the per-second low energy shift of C.

Figure 11:
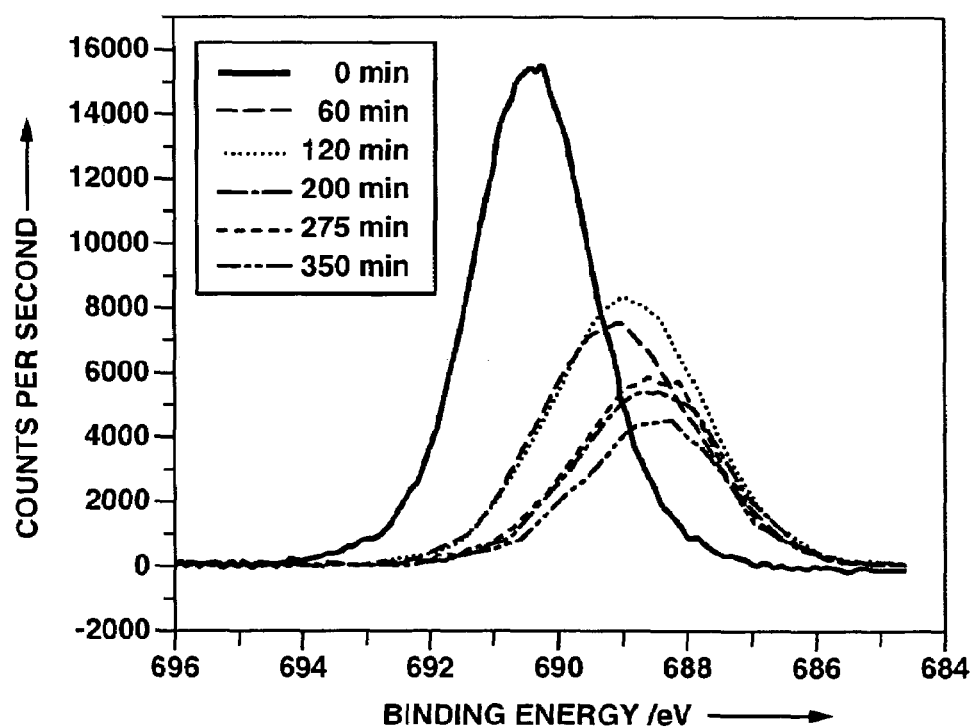
FIG. 11 is a graph showing the change in the per-second binding energy of F with respect to the UV irradiation time.

FIG. 11 is a graph showing the change in the per-second binding energy of F with respect to the UV irradiation time. As FIG. 11 shows, a clear F-atom reduction can be seen, and the binding energy of the F atoms also induces a low energy shift.

These results indicate the following. That is, in UV irradiation of an FAS-SAM in an ultrahigh vacuum state, only the C—F bonds are cleaved specifically. A major change is not discernable in the other bond types. On the other hand, in the UV irradiation of an FAS-SAM in an oxygen-containing state, a large amount of C—C bond cleavage is clearly observed.

Therefore, by combining an XPS thin-film measurement procedure technology and a plurality of surface observation procedures (measurement of the contact angle and surface potential, ellipsometry, and so forth), control of function processing for a functional thin film such as an SAM (such as surface functionalization by means of UV irradiation, for example) is straightforward.

The invention has industrial applicability as a method of observing a monolayer ultraviolet decomposition process that allows real-time information relating to the monolayer surface reaction to be obtained in a straightforward manner when monolayer decomposition patterning is performed by means of ultraviolet rays, as well as to a method of controlling the degree of monolayer surface decomposition and a patterning method that employ this observation method.

While this invention has been described in conjunction with the specific embodiments thereof, it is evident that many alternatives, modifications, and variations will be apparent to those skilled in the art. Accordingly, preferred embodiments of the invention as set forth herein are intended to be illustrative, not limiting. There are changes that may be made without departing from the spirit and scope of the invention.

What is claimed is:

1. A method of controlling a degree of surface decomposition of a monolayer, comprising:
   measuring a structure of a constituent molecule of the monolayer in an ultrahigh vacuum atmosphere and an oxygen-containing atmosphere, respectively, by a molecular structure measuring device during UV irradiation; and
   controlling an ozone concentration accompanying the UV irradiation based on observation results obtained by using the measuring step.

2. A method of patterning a monolayer, comprising: employing the control method according to claim 1.

3. The observation method according to claim 1, the molecular structure measuring device employing X-rays.

4. The observation method according to claim 1, a wavelength of the UV rays being 174 nm or more.

5. The observation method according to claim 1, the monolayer being a self-assembled monolayer.

6. The observation method according to claim 1, the constituent molecule of the monolayer being a compound terminated by a fluorine chain.

7. The observation method according to claim 1, a physical property of a surface of the monolayer also being measured before and after the UV irradiation.

8. The observation method according to claim 7, the surface physical property being a surface potential, thickness or wetting contact angle (water).

* * * * *